(12) United States Patent
Keinänen et al.

(10) Patent No.: US 11,478,144 B2
(45) Date of Patent: Oct. 25, 2022

(54) CONTACT ARRANGEMENT FOR EYE EXAMINING INSTRUMENT, EYE EXAMINING INSTRUMENT AND METHOD OF CONTACTING BETWEEN EYE AND EYE EXAMINING INSTRUMENT

(71) Applicant: Optomed Oyj, Oulu (FI)

(72) Inventors: Alpo Keinänen, Oulu (FI); Ilkka Jolma, Oulu (FI); Markku Virta, Oulu (FI)

(73) Assignee: OPTOMED OYJ, Oulu (FI)

(*) Notice: Subject to any disclaimer, the term of this patent is extended or adjusted under 35 U.S.C. 154(b) by 0 days.

(21) Appl. No.: 17/327,964

(22) Filed: May 24, 2021

(65) Prior Publication Data

US 2021/0401285 A1    Dec. 30, 2021

(30) Foreign Application Priority Data

Jun. 29, 2020 (FI) .......................... 20205692

(51) Int. Cl.
*A61B 3/10* (2006.01)

(52) U.S. Cl.
CPC ........................ *A61B 3/10* (2013.01)

(58) Field of Classification Search
CPC .................................. A61B 3/10; G02C 5/00
USPC ............................................................ 351/219
See application file for complete search history.

(56) References Cited

U.S. PATENT DOCUMENTS

| | | | | |
|---|---|---|---|---|
| 2,002,543 A | * | 5/1935 | Meyrowitz | A61F 9/026 2/440 |
| 2,049,102 A | * | 7/1936 | Baker | A61F 9/028 2/436 |
| 2,896,615 A | * | 7/1959 | Szigeti | A61F 9/02 351/44 |
| 6,637,881 B1 | | 10/2003 | Siminou | |
| 2008/0259274 A1 | | 10/2008 | Chinnock | |
| 2013/0128223 A1 | | 5/2013 | Wood et al. | |

(Continued)

FOREIGN PATENT DOCUMENTS

| | | |
|---|---|---|
| AU | 2011 235 002 | 8/2016 |
| CN | 204797794 | 11/2015 |
| CN | 107708524 | 2/2018 |

(Continued)

OTHER PUBLICATIONS

Chinese Office Action in CN Application No. 202110642151.7, dated Apr. 8, 2022, (English translation attached) (16 pages).

(Continued)

*Primary Examiner* — Collin X Beatty
(74) *Attorney, Agent, or Firm* — Leason Ellis LLP

(57) ABSTRACT

A contact arrangement for an eye examining instrument is located between an eye that is examined and a section of the eye examining instrument, the section is directed toward the eye that is examined. The contact arrangement is disposable, biocompatible with skin and made of biodegradable material. A first side of the contact arrangement is set in contact with the skin around the eye that is examined. A second side of the contact arrangement is attached with a counterpart of the eye examining instrument in a tool-free manner without touching with hands to the contact arrangement, the attachment being releasable, at the section, which is directed toward the eye that is examined.

17 Claims, 12 Drawing Sheets

(56) References Cited

U.S. PATENT DOCUMENTS

2015/0238166 A1    8/2015  Heath et al.
2019/0142636 A1    5/2019  Tedford et al.

FOREIGN PATENT DOCUMENTS

| CN | 208926602 | | 6/2019 |
|---|---|---|---|
| GB | 2378771 | | 2/2003 |
| JP | H1133140 A | * | 2/1999 |
| JP | 2005 017401 | | 1/2005 |
| JP | 2005-168941 | | 6/2005 |
| JP | 2011-508651 | | 3/2011 |
| JP | 2011-515194 | | 5/2011 |
| JP | 2015500732 A | | 1/2015 |
| JP | 2015-229022 | | 12/2015 |
| JP | 2018-501936 | | 1/2018 |
| KR | 102130310 B1 | | 7/2020 |
| WO | WO 01/49166 | | 7/2001 |
| WO | WO 2017/195163 | | 11/2017 |
| WO | WO 2019/143668 | | 7/2019 |

OTHER PUBLICATIONS

European Office Action in EP Application No. 21175254.8-1126, dated Jul. 26, 2022, (10 pages).
Ottenhall Anna et al: "Water-stable cellulose fiber foam with antimicrobial properties for bio based low-density materials", Cellulose, Springer Netherlands, Netherlands, vol. 25, No. 4, Mar. 7, 2018 (Mar. 7, 2018), pp. 2599-2613.

* cited by examiner

CONTACT ARRANGEMENT FOR EYE EXAMINING INSTRUMENT, EYE EXAMINING INSTRUMENT AND METHOD OF CONTACTING BETWEEN EYE AND EYE EXAMINING INSTRUMENT

CROSS-REFERENCE TO RELATED PATENT APPLICATION

This application claims priority from Finnish Patent Application 20205692, filed Jun. 29, 2020, the entire contents of which is incorporated by reference herein as if expressly set forth in its respective entirety herein.

FIELD

The invention relates to a contact arrangement for an eye examining instrument, an eye examining instrument, and a method of contacting between an eye and an eye examining instrument.

BACKGROUND

When a surface of an eye examining instrument such as a fundus camera or ophthalmoscope with a camera is in a skin contract with a patient whose eye is examined, the surface has to be cleaned and disinfected after each patient and/or each examination. Such a cleaning takes time and consumes cleaning tissue and cleaning and disinfecting agent, which may be harmful to both the cleaning person and the environment. Additionally, the cleaning tissue is waste.

In some cases, the eye examining instrument may allow hand-held operation. Then the eye examining instrument is typically compact and easy to align with the eye during the imaging. Such a hand-held eye examining instrument may be suitable for a field use in addition to clinics and hospitals. In the field use, cleaning and disinfecting may become even more challenging because of lack or scarcity of suitable cleaning means. Hence, an improvement would be welcome.

BRIEF DESCRIPTION

The present invention seeks to provide an improvement to cleanness and/or disinfection of the surface of the eye examining instrument that is in contact with a patient.

The invention is defined by the independent claims. Embodiments are defined in the dependent claims.

LIST OF DRAWINGS

Exemplary embodiments of the present invention are described below, by way of example only, with reference to the accompanying drawings, in which FIG. 1A illustrates an example an eye examining instrument seen from side;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1A:
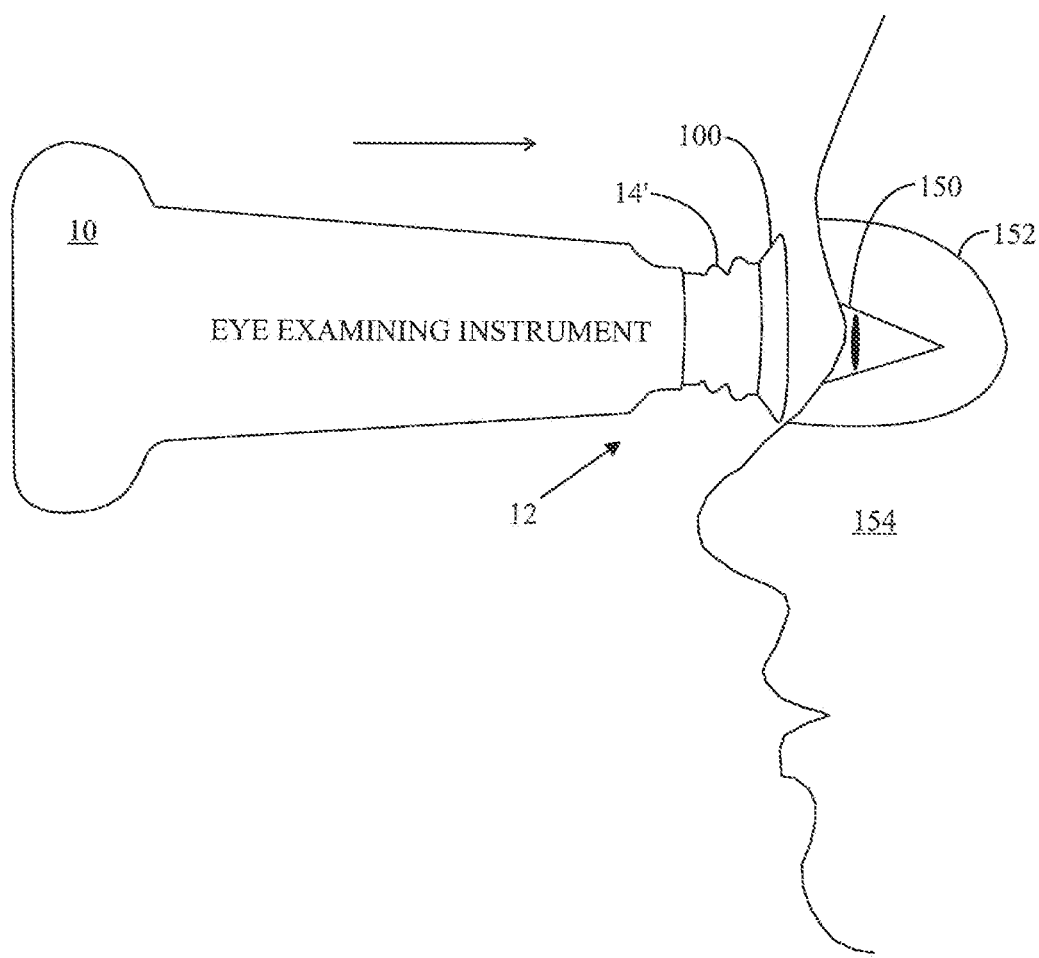
FIG. 1B illustrates an example of the eye examining instrument seen from above.

FIG. 1A illustrates an example of an eye examining instrument 10 seen from side. In this example only one eye 150 of a patient may be examined at a time. The patient may be a human being or more generally a mammal. When the eye 150 of the patient 154 is examined, the eye examining instrument 10 is moved toward the eye 150 such that a contact arrangement 100 is in physical contact with the skin 152 around the eye 150. The skin areas that are at least partly covered in all embodiments may be superonasal, superotemporal, inferonasal and inferotemporal area.

The contact arrangement 100 is located between the eye 150 that is examined and a section 12 of the eye examining instrument 10. The section 12 is the directed toward the eye 150 that is examined in order to move the contact arrangement 100 to touch the skin 152.

Figure 1B:
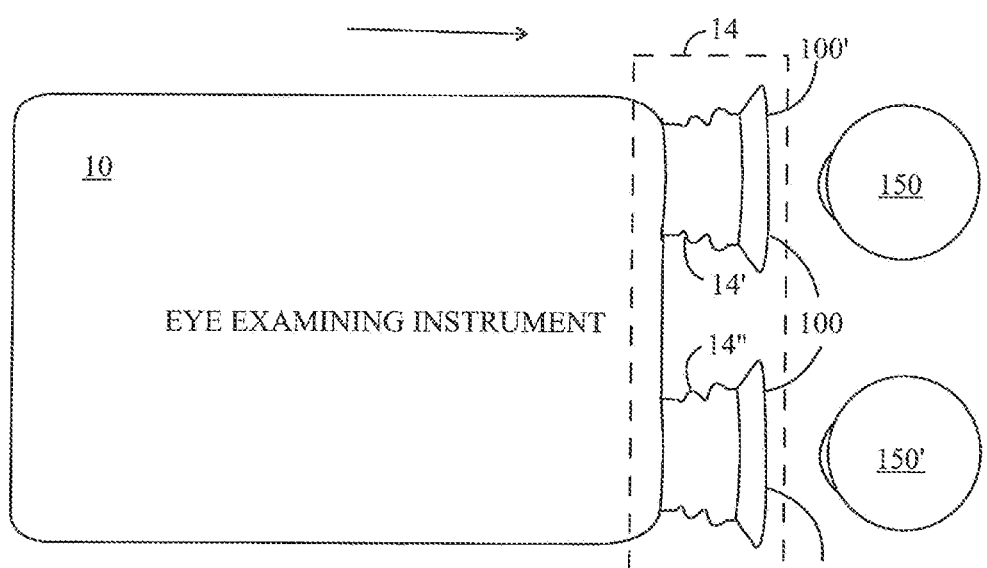

FIG. 1B illustrates an example of an eye examining instrument 10 from above. The contact arrangement 100 of the eye examining instrument 10 of this example can be in a physical contact with both of the eyes 150, 150' of the patient 154 simultaneously. When the eyes 150, 150' of the patient 154 are to be examined, the eye examining instrument 10 is moved toward the eyes 150, 150' such that the contact arrangement 100 is in physical contact with the skin 152 around the eyes 150, 150' of a patient 154 (see FIG. 1A). In an embodiment, the contact arrangement 100 may comprise a pair of separate contact structures 100', 100", one 100' of which is for one eye 150 and another 100" of which is for another eye 150', for contacting the skin 152 around the eyes 150, 150'.

In general, the contact arrangement 100 is disposable, biocompatible with skin and made of biodegradable material. Biocompatible means that the contract arrangement 100 is not harmful or toxic to the skin 152 or living tissue of a human being or another mammal. The contact arrangement 100 is meant to be disposed after a single use or after a use for a single patient 154. The eye examining instrument may refer to an ophthalmoscope, a retinoscope, a corneal microscope, a keratometer, a campimeter, any combination thereof or the like. In an embodiment, the eye examining instrument 10 may capture still or video image of an eye or eyes 150, 150'.

Examine now the embodiment which has the contact arrangement 100 that is for one eye only.

Figure 2A:
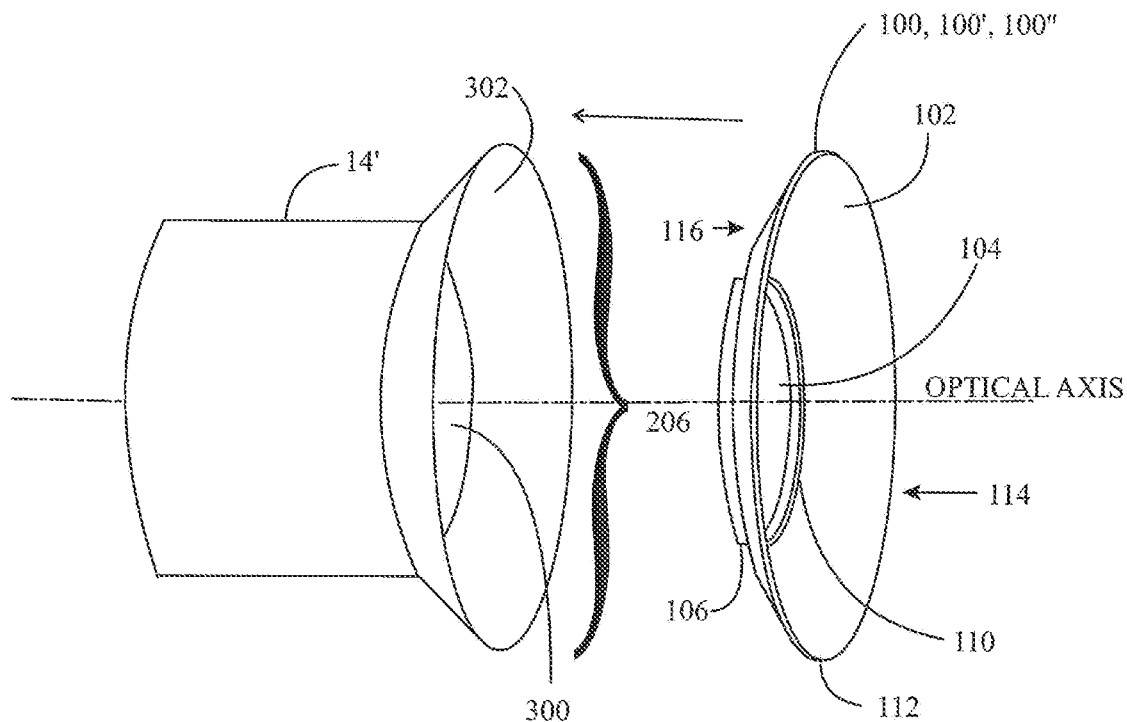
FIG. 2A illustrates an example of attaching a contact arrangement (structure) to an eyecup.

In an embodiment an example of which is illustrated in FIGS. 1A and 2A, the eye examining instrument 10 may comprise an eyecup arrangement 14 that has a single eyecup 14', which is meant for one of the eye 150, 150'.

In an embodiment an example of which is illustrated in FIG. 2A in association with FIG. 1A, the contact arrangement 100, which comprises in this embodiment a contact structure 100', may be attached with the eyecup 14'. Then another contact structure 100" similar to the contact structure 100' may be attached with another eyecup 14" in a similar manner (see FIG. 1B).

The contact structure 100' of the example of FIG. 2A comprises a rim 102 around an aperture 104, through which an examination of the eye 150 is performed. That is, the contact structure 100' may be circular with a shape of a ring to a certain extent. A first side 114 of the rim 102 may have a shape of a surface of the skin 152 around the eye 150 in order to match the curvature of the skin 152 at least approximately. The rim 102 may be flexible in order to alter its shape under pressure and adapt to a shape of a surface of the skin 152 around the eye 150. A surface of a first side 114 of the rim 102 is set in contact with the skin 152 around the eye 150 that is examined. The first side 114 may be concave. A surface of a second side 116 of the contact arrangement 100 is applied and attached with a counterpart 206 of the eyecup 14', which is in this embodiment considered the section 12 of the eye examining instrument 10 directed toward the eye 150 that is examined. The second side 116 may be convex in a similar manner to the concaveness of the first side 114 if the eyecup 14' has such a shape. The attachment is performed in a tool-free and may also be performed in a hands-free manner. The attachment is performed without touching with hands to the contact arrangement 100. The attachment is releasable. In an embodiment, the attachment may be released with hands and/or with a tool. In an embodiment, the attachment may be released by a tool-free and hands-free manner. The counterpart 206 may comprise a rim 302 of the eyecup 14'.

As a mass of the contact structure 100' is small because the contact structure 100 is thin, the contact structure 100 will remain in place attached to the eyecup 14' easily. The mass of the contact structure 100' may be similar to a corresponding piece of paper or board.

In an embodiment, the biodegradable material of the contact structure 100' comprises cellulose and/or recyclable plastic.

Figure 2B:
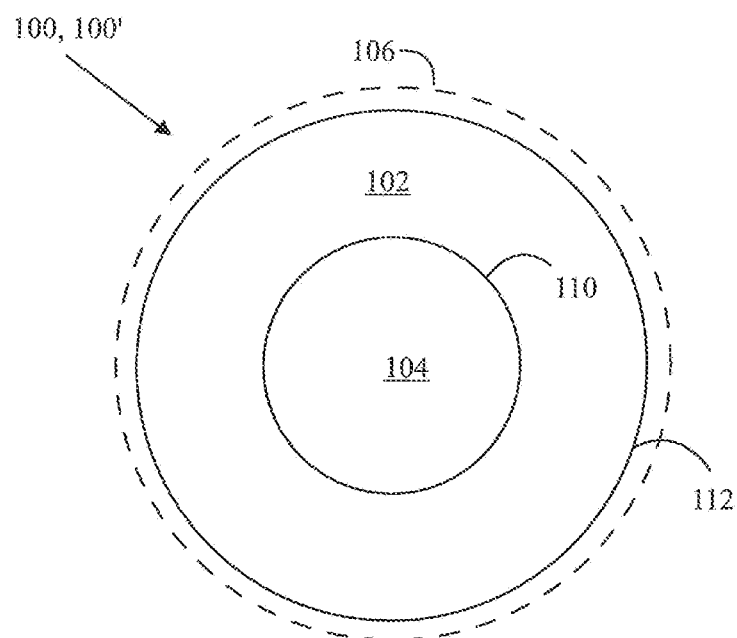
FIG. 2B illustrates an example of a contact structure.
Figure 2C:
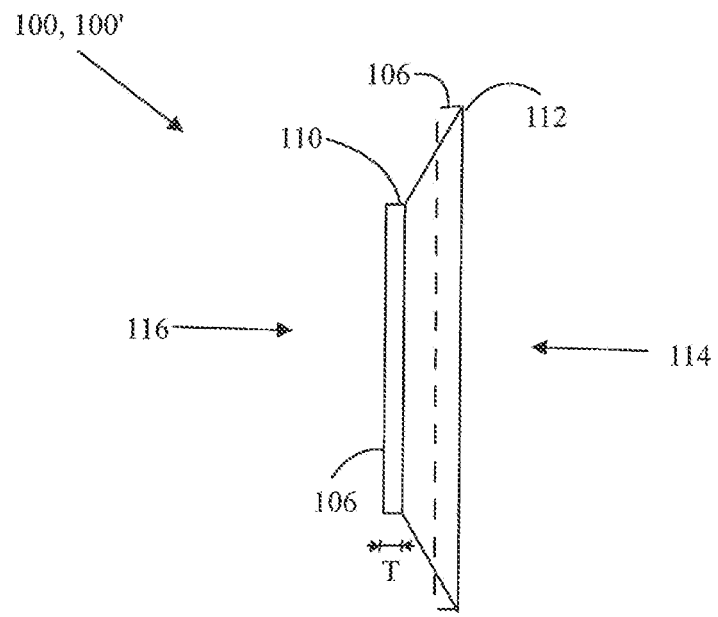
FIG. 2C illustrates an example of a contact structure.

FIG. 2B illustrates the contact structure 100' from the front in a direction parallel to the optical axis of an optical use of the contact structure 100' in the eye examining instrument 10. FIG. 2C illustrates the contact structure 100' from a side in a direction perpendicular to that of FIG. 2B.

In an embodiment examples of which are illustrated in FIGS. 2A and 2C, the contact structure 100' may comprise a wall structure 106 that may continue fully or piece-wisely around an inner edge 110 of the rim 102, the inner edge 110 being in conjunction with the aperture 104 (the inner edge 110 can also be seen in FIG. 2B). The wall structure 106 extends outwards from the second side 116 of the rim 102 opposite to said first side 114. The wall structure 106 is configured to enter or be inserted in a hole 300 of the eyecup 14', the counterpart 206 of the contact arrangement 100 comprising the hole 300. The eye 150 is examined through the hole 300 using the eye examining instrument 10 because the aperture 104 and the hole 300 overlap. The aperture 104 of the contact structure 100' has at least approximately a same shape as a hole 300 through the eyecup 14', and the aperture 104 has an area that is smaller than or equal to that of the hole 300 of the eyecup 14'.

In an embodiment, an outer diameter of the wall structure 106 and an inner diameter of the hole 300 may be matched with each other for a connection based on friction. The matching may be tight.

Figure 3:
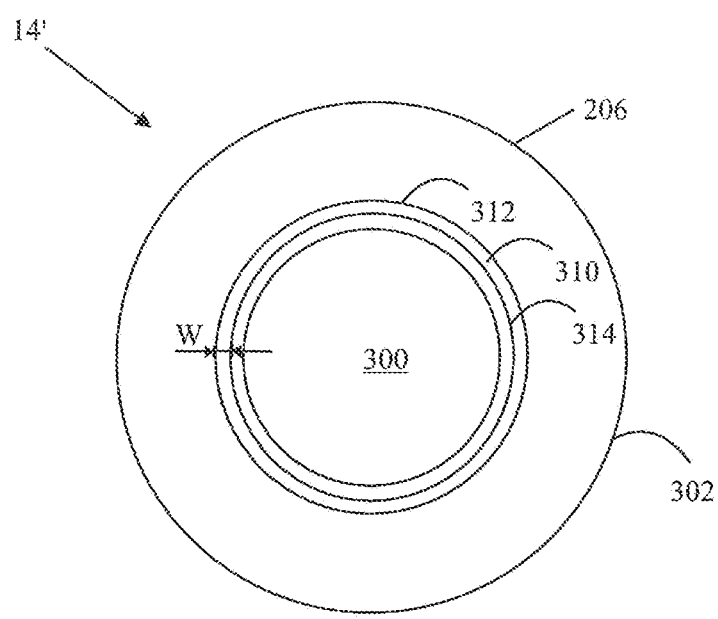
FIG. 3 illustrates an example of an eyecup with a slit.

In an embodiment an example of which is illustrated in FIG. 3, the wall structure 106 around the inner edge 110 may be inserted in a round slot 310 of the counterpart 206. In an embodiment of FIG. 3, an inner diameter of the wall structure 106 and an outer surface 312 of the slot 310 may be tightly matched with each other for a connection based on friction.

In an embodiment of FIG. 3, an outer diameter of the wall structure 106 and an inner surface 314 of the slot 310 may be matched with each other for a connection based on friction. The matching may be tight.

In an embodiment of FIG. 3, a width W of the slot 310 and a thickness T of the wall structure 106 may be matched to each other in order to form a physical contact therebetween that results in a friction attachment. These kinds of friction attachments require stronger force to remove the contact structure 100' from the eyecup 14' than maximum force caused by gravitation to the contact structure 100'. The direction of the gravitation is the parallel to the optical axis of the aperture 104 in a situation where the contact structure 100' may freely fall down if detached from the attachment.

In an embodiment examples of which are illustrated in FIGS. 2B and 2C, the contact structure 100' may comprise an alternative or additional wall structure 106 (see the dashed line) that may continue fully or piece-wisely around an outer edge 112 of the rim 102. This wall structure 106 also extends outwards from the second side 116 of the rim 102 opposite to said first side 114. The wall structure 106 may be configured to contain and attach with an outer circumference of the eyecup 14', the counterpart 206 of the contact arrangement 100 comprising the outer circumference of the eyecup 14'. The wall structure 106 of the contact structure 100' has at least approximately same shape as the outer circumference of the eyecup 14', and the wall structure 106 of the contact structure 100' is matched with the outer circumference of the eyecup 14'.

Figure 4A:
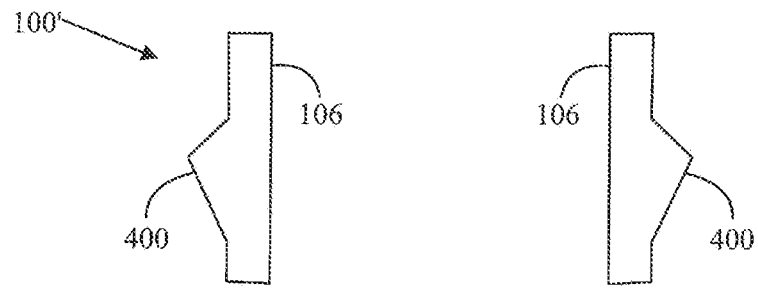
FIG. 4A illustrates an example of a wall structure with a mechanical quick-coupling structure.
Figure 4B:
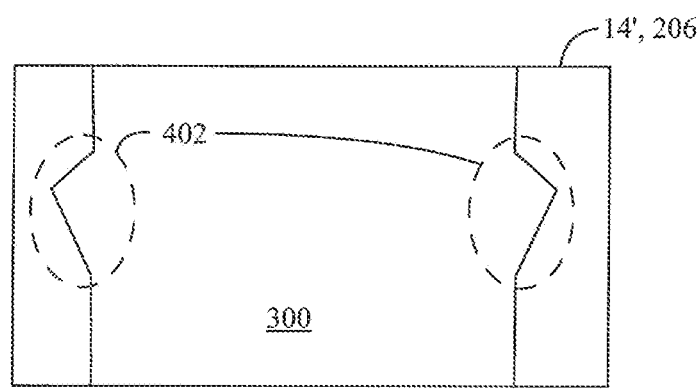
FIG. 4B illustrates an example of an eyecup with a mechanical quick-coupling pair for the mechanical quick-coupling structure of the wall structure.

FIG. 4A illustrates an example of a cross section of the wall structure 106 around the inner edge 110 of the contact structure 100' that may comprise a first mechanical quick-coupling structure 400. FIG. 4B illustrates an example of a cross section of the eyecup 14' with a first mechanical quick-coupling pair 402 which is for the first mechanical quick-coupling structure 400. The first mechanical quick-coupling pair 402 may reside within the hole 300. In an embodiment, the wall structure 106 of the first mechanical quick-coupling structure 400 may be coupled mechanically with a first mechanical quick-coupling pair 402 that the eyecup 14' as the counterpart 206 comprises. The shape and size of the quick-coupling structure 400 and the quick-coupling pair 402 may vary a lot. In this manner, the contact structure 100' and the eyecup 14' may be coupled together in a manner stronger than the friction only.

Figure 4C:
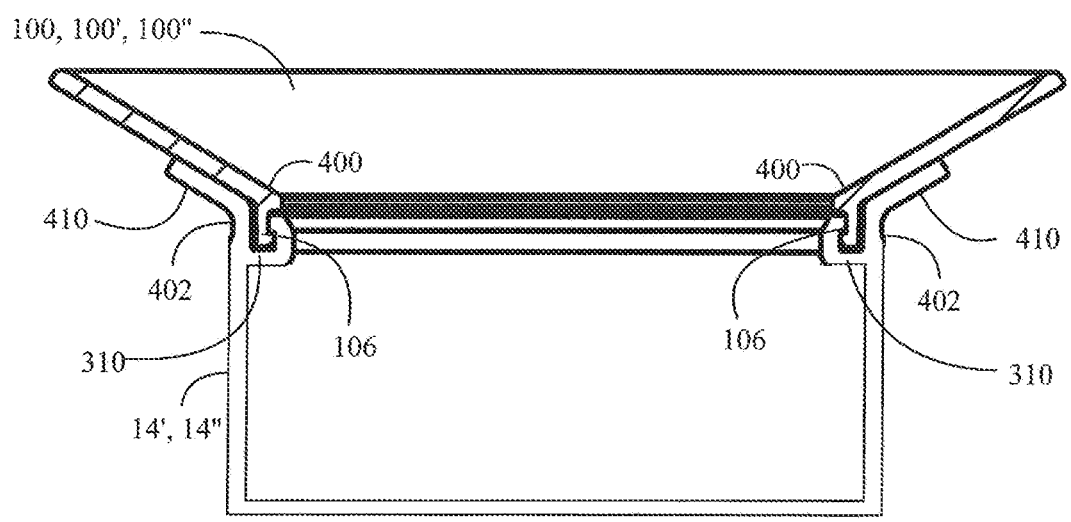
FIGS. 4C and 4D illustrate additional examples of mechanical quick-coupling structure and their mechanical quick-coupling pairs.
Figure 4D:
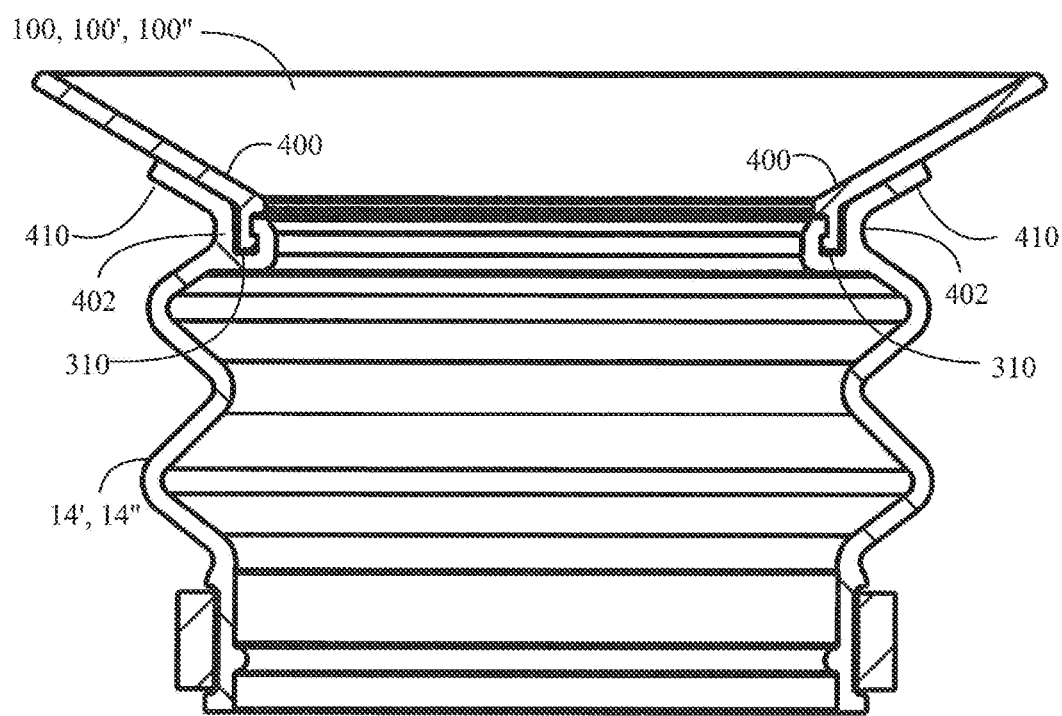

FIGS. 4C and 4D illustrate additional examples of mechanical quick-coupling structures 400 and their mechanical quick-coupling pair 402. In an embodiment, the eyecup 14', 14" may comprise a support rim 410 for the contact structure 102, 102'.

In an embodiment, the wall structure 106 may, together with its counterpart, i.e. the hole 300 and/or the slot 310, cause the aperture 104 to overlap with the hole 300 of the eyecup 14' in response to contact therebetween such that an examination of the eye 150/150' may be performed through the hole 300 of the eyecup 14'.

In an embodiment examples of which are shown in FIGS. 1B and 5A, the eye examining instrument 10 may comprise two eyecups 14', 14", one for one eye and another for another eye. If the eyecups 14', 14" are separate, application of the contact structures 100' to each of them may be similar to what is explained relating to FIGS. 1A, 2A, 2B, 2C, 3, 4A and 4B.

Figure 5:
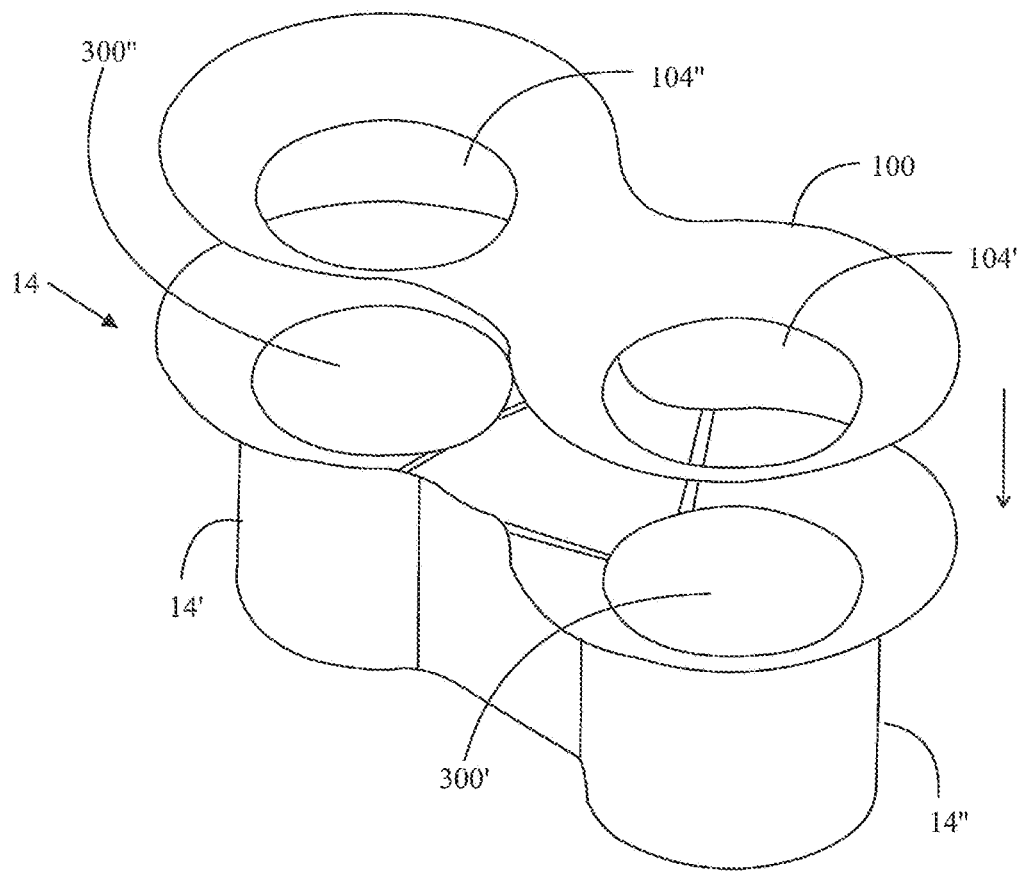
FIG. 5 illustrates an example of an eyecup arrangement for both eyes.

In an embodiment an example of which is illustrated in FIG. 5, the eyecup arrangement 14 may comprise two eyecups 14', 14" that are integrated together, and the eyecup arrangement 14 covers both eyes 150 simultaneously.

Even in this case, the contact arrangement 100 may comprise one contact structure 100' that is attached with one eyecup 14', and another contact arrangement 100", that is attached with another eyecup 14", each of the contact structures 100', 100" being similar to that explained in association with and shown in FIGS. 2A, 2B, 2C, 4A and 4B.

Figure 6:
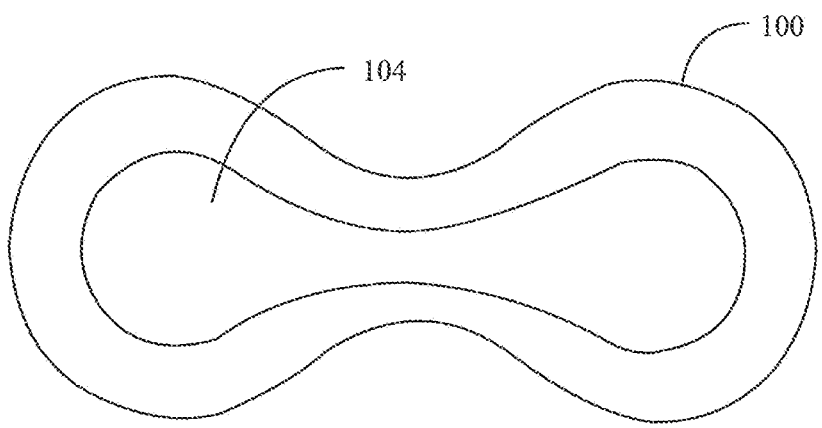
FIG. 6 illustrates an example of a contact structure for the eyecup arrangement meant for both eyes.

However, as the eyecup arrangement 14 of FIG. 5 may cover both eyes simultaneously, the contact arrangement 100 that will be in a physical contact with both of the eyes 150 likewise simultaneously may be attached to the eyecup arrangement 14. That is, the eyecup arrangement 14 and the contact arrangement 14 are common to both eyes. The contact arrangement 100 be attached with the eyecup arrangement 14 in a similar manner to the attachment between the contact structure 100' and the eyecup 14' explained in association with FIGS. 2A, 2B, 2C, 4A and 4B. That is, the attachment may be based on friction and/or mechanical quick-coupling. In a similar manner, the holes 300', 300" of the eyecup arrangement 14 and the apertures 104', 104" of the contact arrangement 100 may be directed to each other based on the attachment. Instead of two apertures 104', 104", the contact arrangement 100 may comprise only one aperture 104 as shown in FIG. 6.

Figure 7:
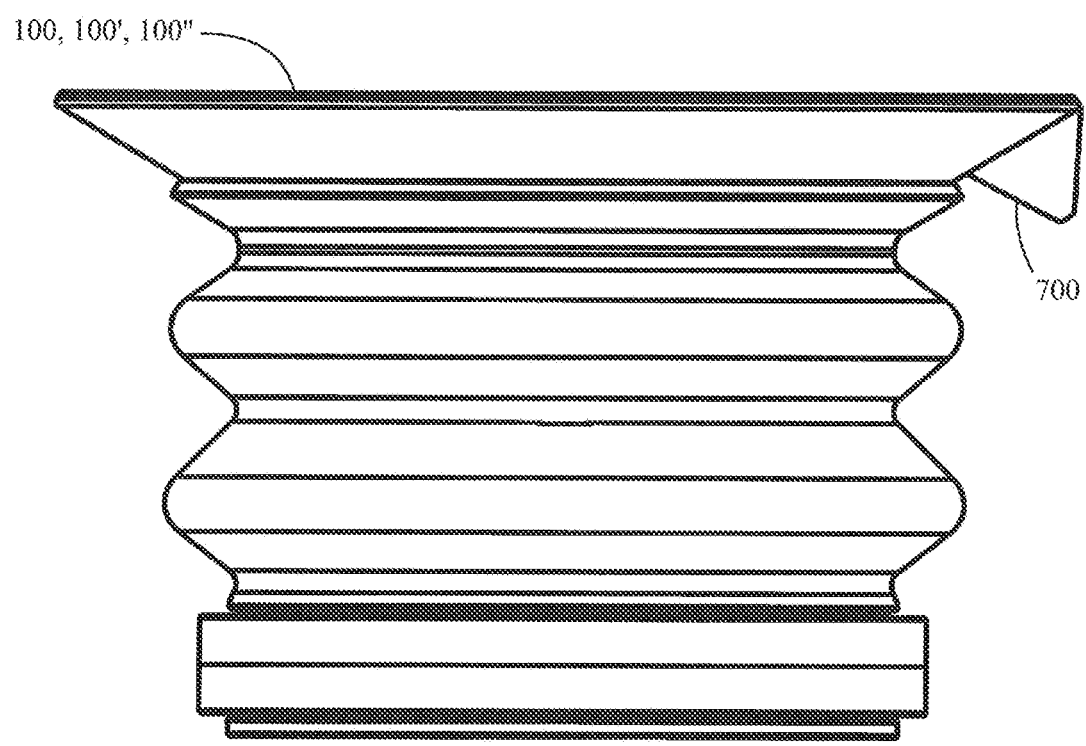
FIG. 7 illustrates an example of removing means of the contact arrangement.

FIG. 7 illustrates an example of removing structure 700 of the contact arrangement 14 or the contact structure 14', 14". The removing structure 700 may comprise an extension projecting outwards from the contact arrangement 100 or the contact structure 100', 100". The removing structure 700 may have size that is easy to take a grip with fingers, for example. A shape of the removing structure 700 may be at least approximately a circle, a rectangle or a triangle, for example.

Figure 8A:
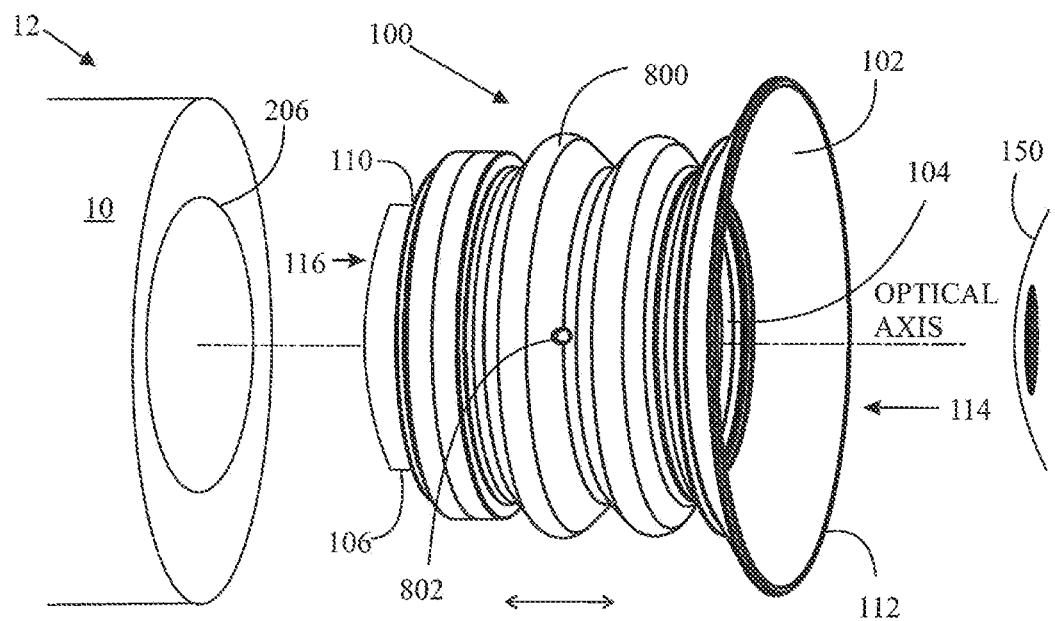
FIG. 8A illustrates an example of a contact arrangement that replaces an eyecup.
Figure 8B:
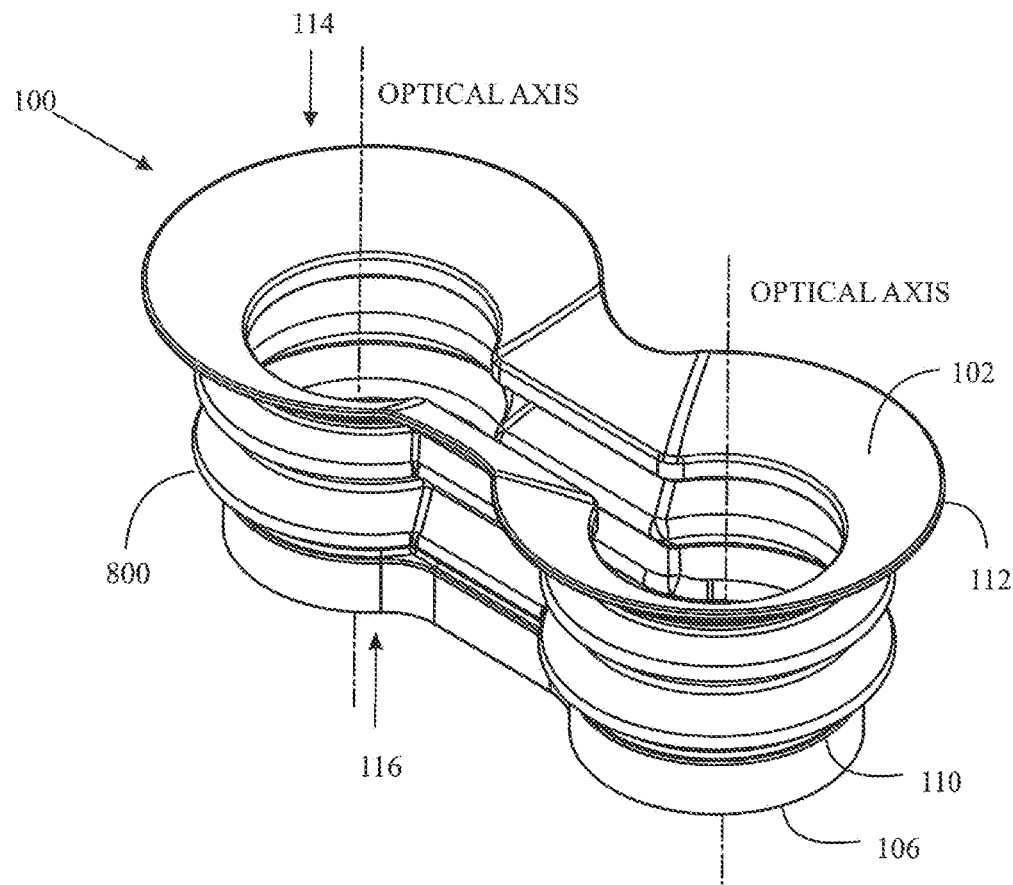
FIG. 8B illustrates an example of a contact arrangement that replaces an eyecup arrangement for both eyes.

In an embodiment examples of which are illustrated in FIGS. 8A and 8B, the contact arrangement 100 may replace the eyecup arrangement 14. That is, the contract arrangement 100 itself acts as an eyecup arrangement. In FIG. 8A the contact arrangement 100 is similar to and may replace the eyecup arrangement 14, which comprises only one eyecup 14'. In FIG. 8B the contact arrangement 100 is similar to and may replace the eyecup arrangement 14 that is common to both eyes.

In an embodiment, the contact arrangement 100 of FIGS. 8A and 8B may have at least one folding 800 for controlling an impact, when the rim 102 of the contact arrangement 100 touches the skin 152 around the eye 150, and acting like a spring and/or an attenuator in order to keep a proper physical contact between the rim 102 and the skin 152 when the eye examining instrument 10 moves forward and backward, and also sideways caused by movement of the patient 154 and particularly if/when a hand-held eye examining instrument is used.

In an embodiment, the first side 114 may be concave in order fit on an eye. The second side 116 may be convex in a similar manner corresponding to the concaveness of the first side 114. As mass of the contact arrangement 100 is small because the contact arrangement 100 is thin, the contact arrangement 100 will remain in place attached to the eye examining instrument 10 easily. The mass of the contact arrangement 100 may be at least about the same as a corresponding piece of paper or board.

The contact arrangement 100 of the embodiments of FIGS. 8A and 8B may be flexible in order to alter its shape under pressure and adapt to a shape of a surface of the skin 152 around the eye 150.

In an embodiment, the contact arrangement 100 of FIGS. 8A and 8B may include an air hole 802 which may let air move into and out of the aperture 102, which is a cavity within the contact arrangement 100, in response to shortening and lengthening of the contact arrangement 100 when the eye examining instrument 10 moves back and forth while keeping the physical contact between the rim 102 and the skin 152.

As earlier explained, also this contact arrangement 100 may comprise a wall structure 106 that is configured to continue fully or piece-wisely around at least one of the following: an inner edge 110 of the contact arrangement 100 or an outer edge 112 of the rim 102, the inner edge 110 being in conjunction with the aperture 104 and the outer edge 112 being opposite to the inner edge 110 in a lateral direction. The wall structure 106 may extend outward from a surface the second side 116 of the contact arrangement 100 opposite to said first side 114. The wall structure 106 may be attached with a counterpart 206 of the eye examining instrument 10 in a tool-free releasable manner at the section 12, which is directed toward the eye 150 that is examined. This attachment may be performed as earlier explained. However, with the contact arrangement 100 of FIG. 8A or 8B, the counterpart 206 is not in the eyecup like in FIGS. 2A, 3 and 5 but in the housing of the eye examining instrument 10.

The attachment between the contact arrangement 100 and the eye examining instrument 10 is performed in a tool-free and hands-free manner. That is, the contact arrangement 100 requires no contact with a hand or with a tool hold by a hand of a person doing the attachment. The examining instrument 100 may be hold by the person doing the attachment. The attachment is releasable. In an embodiment, the attachment may be released with hands and/or with a tool. In an embodiment, the attachment may be released a tool-free and hands-free manner. During the release, hands of the person performing the release may be covered with disposable gloves (medical personnel typically wear such gloves when performing examinations).

Figure 9A:
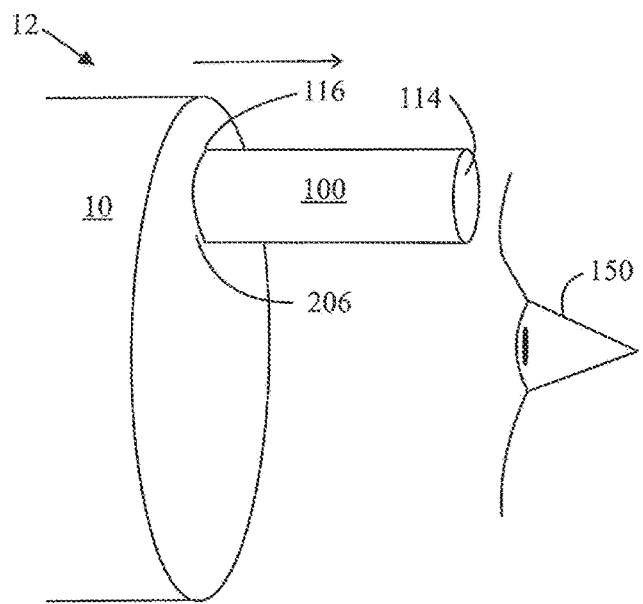
FIG. 9A illustrates an example of a contact arrangement that replaces a support rod of the eye examining instrument.

FIGS. 8A and 8B illustrate examples of a support rod 900 and the contact arrangement 100. In an embodiment of FIG. 9A the support rod 900 (see FIG. 9B) is fully replaced with a contact arrangement 100 that has a shape of the support rod 900. The support rod 900 is moved toward the forehead of the patient and set in a firm contact with the forehead in order to perform the examination.

Figure 9B:
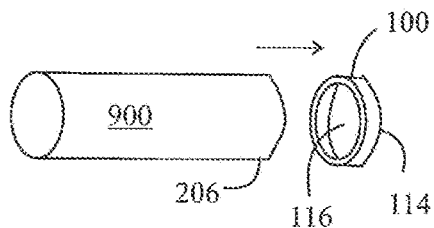
FIG. 9B illustrates an example of a contact arrangement attachable to a support rod of the eye examining instrument.

In an embodiment of FIG. 9B, the contact arrangement 100 may comprise a tube structure or the like that is closed at one end by a bottom layer, which has the first side 114 and the second side 116. The contact arrangement 100 may be like a sock into which the rod 900 is inserted fully or only partly from one end.

When the eye examining instrument 10 is approaching the eye 150 a surface of the first side 114 will touch the skin around the eye 150 and the eye examining instrument 10 will remain in a constant location with respect to the eye 150. The second side 116 of the contact arrangement 100 is attached, at the section 12, with a counterpart 206 of the eye examining instrument 10 in a tool-free and hands-free manner, the attachment being releasable and at least potentially based on friction. Then the eye examining instrument 10 may perform a measurement of intraocular pressure, for example.

Also in the embodiments of FIGS. 8A and 8B, the contact arrangement 100 is disposable and made of biodegradable material. The contact arrangement 100 is meant to be disposed after a single use or after a use for a single patient 154.

In general, the biodegradable material of the contact arrangement 100 in all embodiments comprises cellulose and/or recyclable plastic. That is why it is disposable and made of biodegradable material that is decomposed by microbes, which reduces pollution and simplifies waste processing. The biodegradable material may be porous, which makes it light. The biodegradable material may comprise waterstable cellulose foam such as cellufoam which may be mechanically strong and antimicrobial. A purpose of the contact arrangement 100 of the embodiments of FIGS. 2A to FIG. 8B may also be to keep out extraneous light in the optical examination.

The disposable contact arrangement 100 does not require cleaning and consumes no cleaning tissue or cleaning and disinfecting agent thereby avoiding harm posed to both the cleaning person and the environment. The contact arrangement 100 makes also the field use easier.

Figure 10A:
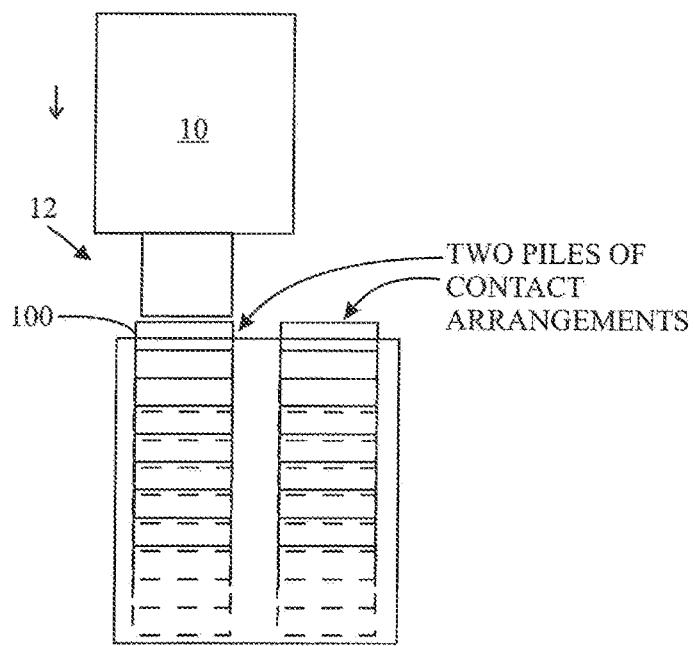
FIG. 10A illustrates an example of piles of contact arrangements that can be attached to the eye examining instrument one after a previous has been used.
Figure 10B:
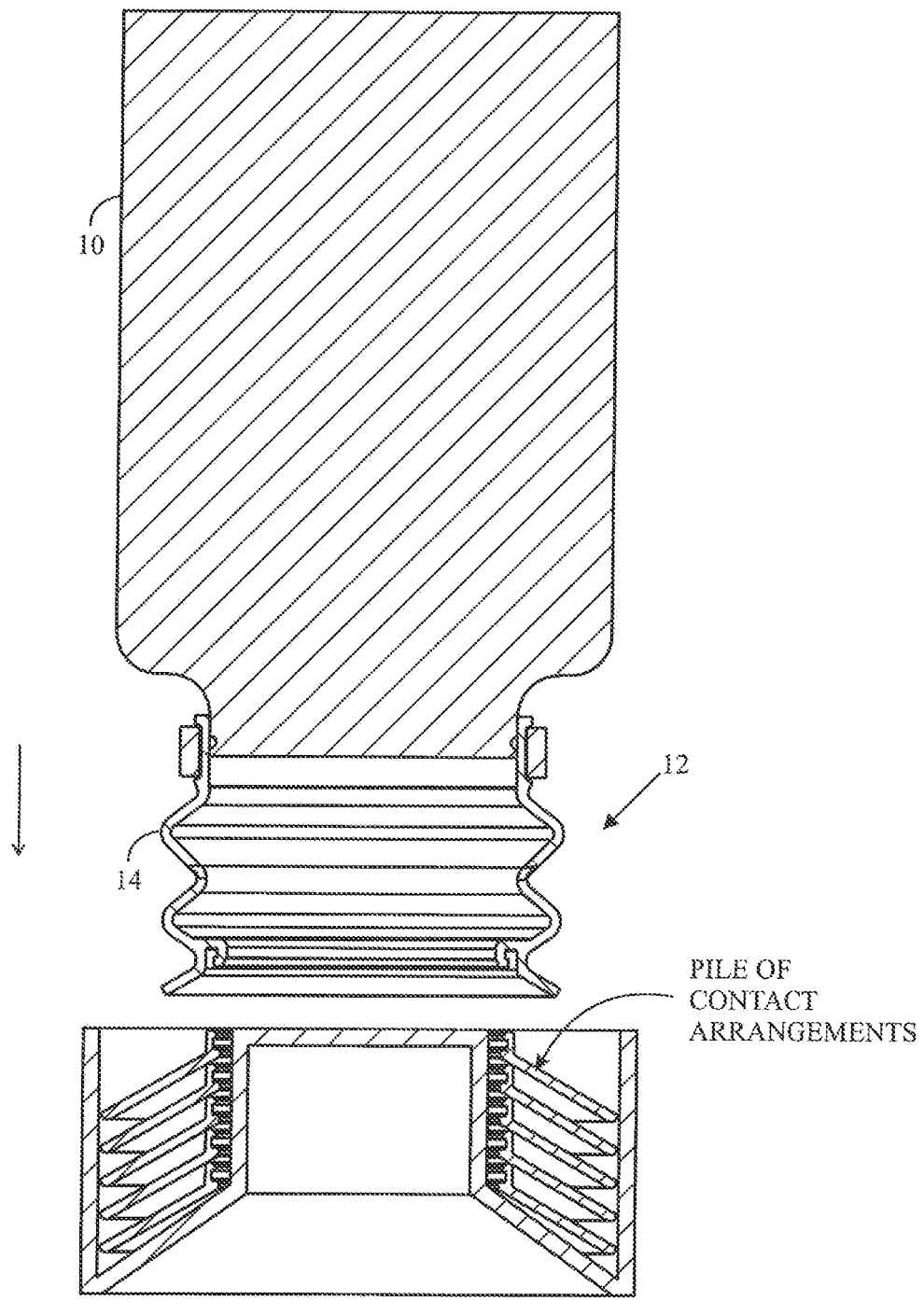
FIG. 10B to 10D illustrates an example how to collect a contact arrangement from the piles of contact arrangements and attach it to the eye examining instrument.

FIG. 10A illustrates an example where the contact arrangements 100 are in a pile one on another. FIG. 10B illustrates an example where the eye examining instrument 10 is moved toward the pile of the contact arrangements 100 such that the section 12, which is in this example an eyecup 14, touches the pile.

Figure 10C:
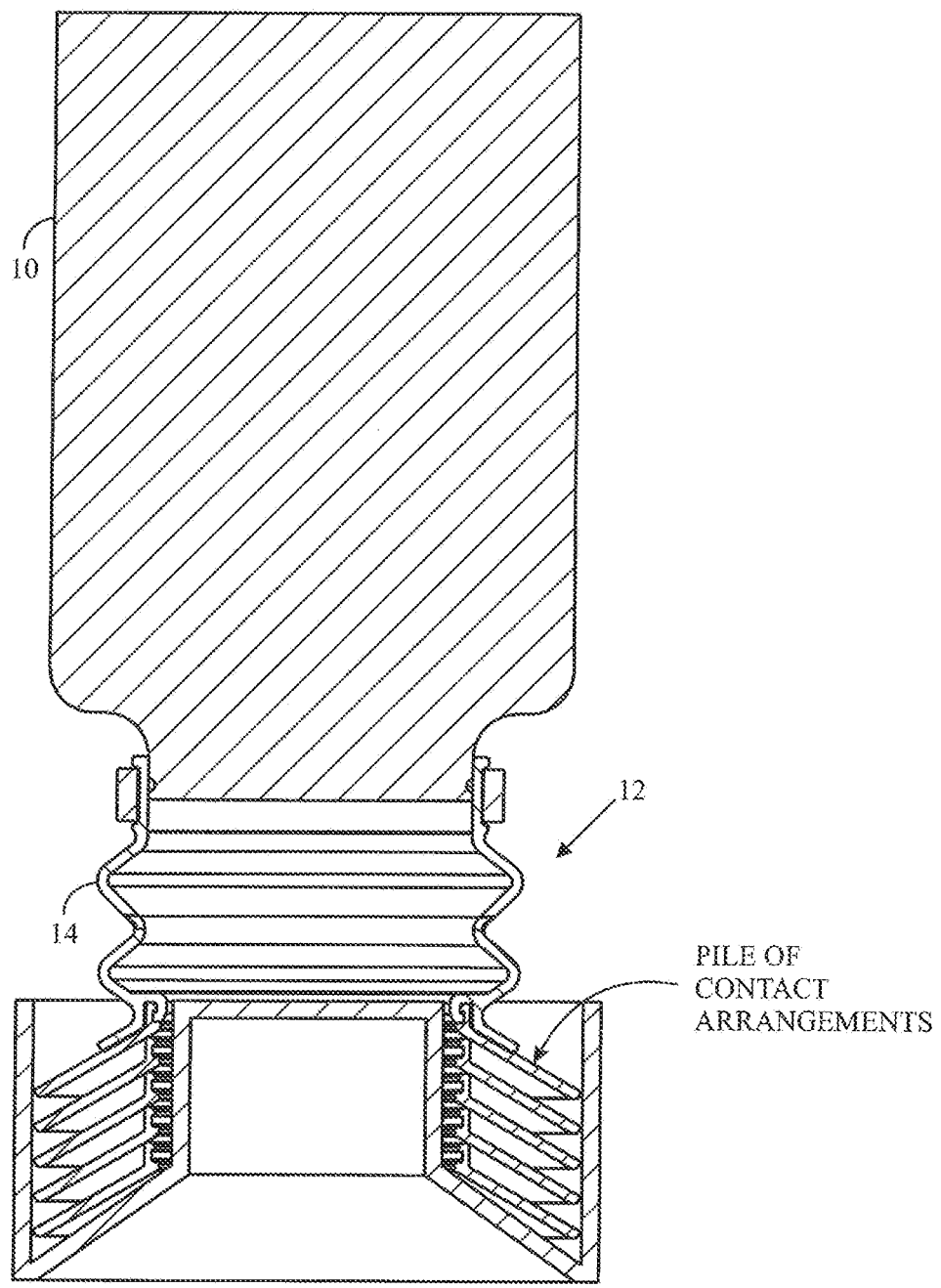

FIG. 10C illustrates an example where the contact arrangement 100 that is at the top of the pile is about to attach or has attached to the counterpart 206 of the eye examining instrument 10. In general, the counterpart 206 may be the housing of the eye examining instrument 10 or the eyecup 14'. It is also possible that a contact arrangement 100 that is meant for both eyes 150, 150' is attached in a similar manner to the eye examining instrument 10 or to the eyecup arrangement 14 that is also meant for both eyes 150, 150'.

Figure 10D:
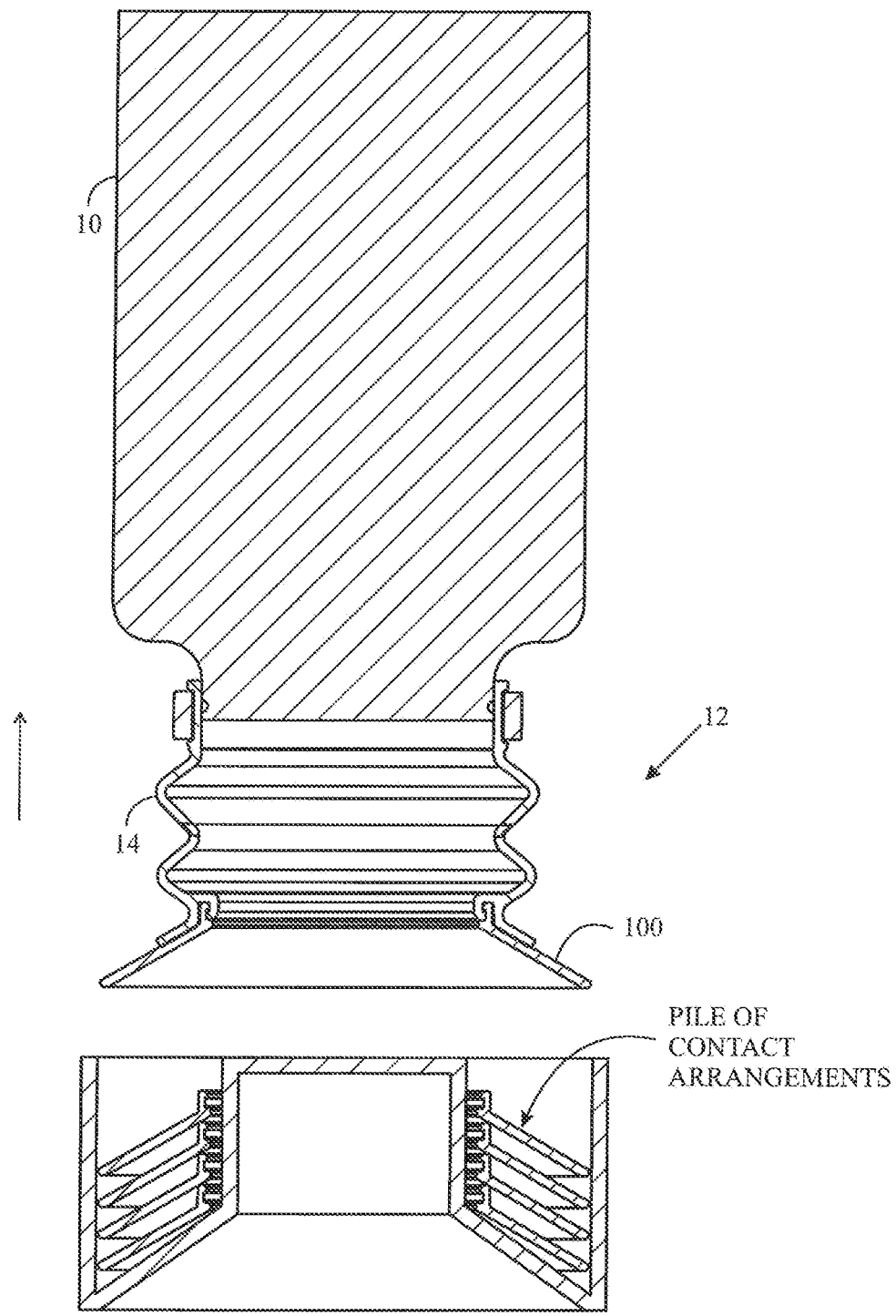

FIG. 10D illustrates an example where the eye examining instrument 10 with one of the contact arrangements 100 is lifted from the pile of contact arrangements 100.

In this manner, each contact arrangement 100 may be attached with the eye examining instrument 10 without touching the contact arrangements 100. This kind of attachment procedure allows a clean contact arrangement 100 to touch a patient's skin 152 around the eye(s) 150, 150'.

Figure 11:
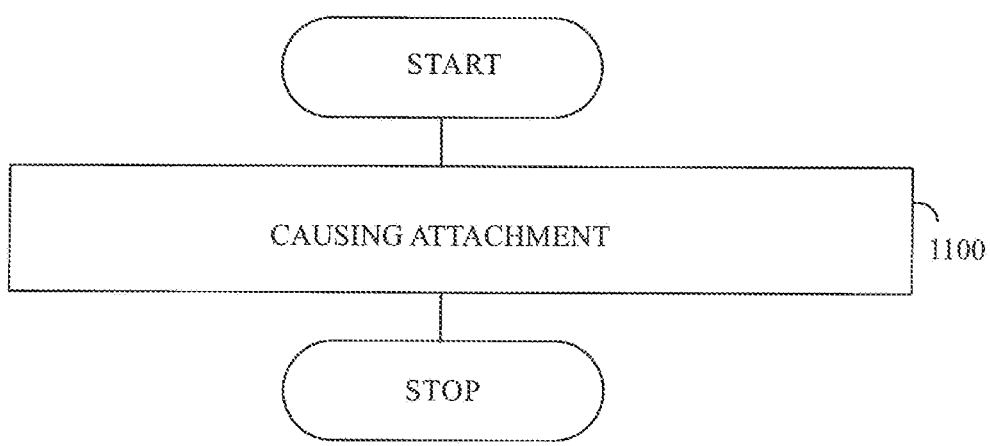
FIG. 11 illustrates of an example of a flow chart of a measuring method of contacting between an eye and an eye examining instrument.

FIG. 11 is a flow chart of the measurement method. In step 1100, an attachment, which is releasable and performed in a tool-free manner, is caused between a second side 116 of a disposable contact arrangement 100 of biodegradable material that is biocompatible with skin and a counterpart 206 of the eye examining instrument 10 without touching with hands to the contact arrangement 100 at a section 12 of the eye examining instrument 10 directed toward the eye 150 that is examined, in response to a force pressing the contact arrangement 100 and the counterpart 206, which have compatible shapes, in contact with each other, for locating the contact arrangement 100 between the eye 150 that is examined and the section 12 of the eye examining instrument 10 and setting a first side 114 of the contact arrangement 100 in contact with the skin 152 around the eye 150 that is examined.

As shown in FIGS. 10B to 10D and explained in above with FIG. 11, the eye examining instrument 10 is used to pick up one that is on the top of the pile of the contact arrangements 100. The picking up may be performed from a package of the contact arrangements 100. When the contact arrangement 100 is attached to the eye examining instrument 10, examination may be performed. After the examination, the contact arrangement 100 can be removed from the eye examining instrument 10 and discarded in a waste bin. A new contact arrangement 100 may be attached by repeating the routine.

It will be obvious to a person skilled in the art that, as technology advances, the inventive concept can be implemented in various ways. The invention and its embodiments are not limited to the example embodiments described above but may vary within the scope of the claims.

What is claimed is:

1. An eye examining system comprising:
an eye examining instrument;
a pile of stacked contact arrangements, for the eye examining instrument, wherein the each contact arrangement is configured to be located between an eye that is examined and a section of the eye examining instrument, the section being directed toward the eye that is examined; each contact arrangement including:
a first side of the contact arrangement is configured to be set in contact with the skin around the eye that is examined;
a second side of the contact arrangement is configured to be attached with a counterpart of the eye examining instrument in a tool-free manner without touching with hands to the contact arrangement, the attachment being releasable, at the section, which is directed toward the eye that is examined;

wherein the contact arrangement, which is disposable, biocompatible with skin and made of biodegradable material, comprises a rim around an aperture, through which an examination of the eye is performed, the rim being flexible in order to alter its shape under pressure and adapt to a shape of a surface of the skin around the eye;

wherein the second side of the contact arrangement is configured to be applied to an eyecup arrangement that comprises the counterpart of the eye examining instrument and that is the section directed toward the eye that is examined;

wherein the aperture of the contact arrangement has a same shape as a hole through the eyecup arrangement, and the aperture has an area that is smaller than or equal to that of the hole of the eyecup arrangement; and a wall structure is, together with its counterpart, configured to cause the aperture to overlap with the hole of the eyecup arrangement in response to contact therebetween, an examination of the eye being performed through the hole of the eyecup arrangement;

wherein the contact arrangement is formed of porous and waterstable cellulose and the contact arrangement includes at least one air hole that is configured to let air move in and out of the aperture;

wherein each contact arrangement is configured to lift from the pile of contact arrangements without touching with hands to the contact arrangement being lifted.

2. The eye examining system of claim 1, wherein a first side of the rim of the contact arrangement is configured to be set in contact with the skin around the eye that is examined; and the second side of the rim of the contact arrangement is configured to be attached with a counterpart of the eye examining instrument.

3. The eye examining system of claim 1, wherein the contact arrangement comprises the wall structure that is configured to continue around at least one of the following: an inner edge of the rim or an outer edge of the rim, the inner edge being in conjunction with the aperture, and the outer edge being opposite to the inner edge in a lateral direction;

the wall structure is configured to extend from the second side of the rim opposite to said first side; and the wall structure is configured to attach with a counterpart of the eye examining instrument in a tool-free releasable manner at the section, which is directed toward the eye that is examined.

4. The eye examining system of claim 3, wherein the wall structure around the inner edge is configured to be inserted in a hole of the counterpart, an outer diameter of the wall structure and an inner diameter of the hole being matched with each other for a connection based on friction.

5. The eye examining system of claim 4, wherein the wall structure around the inner edge comprises a first mechanical quick-coupling structure, which is configured to couple mechanically with a first mechanical quick-coupling pair that the counterpart comprises.

6. The eye examining system of claim 4, wherein the wall structure around the inner edge is configured to insert in a round slot of the eyecup arrangement, an inner diameter of the wall structure and an outer surface of the slot being matched with each other in for a connection based on friction.

7. The eye examining system of claim 4, wherein the wall structure comprises a mechanical quick-coupling structure, which is configured to attach with a mechanical quick-coupling pair that the eyecup arrangement comprises.

8. The eye examining system of claim 3, wherein the wall structure around the inner edge is configured to be inserted in a round slot of the counterpart, an inner diameter of the wall structure and an outer surface of the slot being matched with each other for a connection based on friction.

9. The eye examining system of claim 8, wherein the wall structure comprises a mechanical quick-coupling structure, which is configured to attach with a mechanical quick-coupling pair that the eyecup arrangement comprises.

10. The eye examining system of claim 8, wherein the wall structure around the inner edge comprises a first mechanical quick-coupling structure, which is configured to couple mechanically with a second mechanical quick-coupling structure that is part of the counterpart.

11. The eye examining system of claim 3, wherein the wall structure around the outer edge of the contact arrangement is configured to extend over and mechanically attach with an outer edge of the eyecup arrangement, an inner diameter of the wall structure and an outer diameter of the hole of the eyecup arrangement being matched with each other for a connection based on friction.

12. The eye examining system of claim 1, wherein the material of the contact arrangement comprises cellulose and/or recyclable plastic.

13. The eye examining system of claim 1, further including at least one folding that is disposed between the first side and the second side, wherein the air hole is disposed within the at least one folding.

14. The eye examining system of claim 13, wherein the at least one folding is configured such that the at least one folding acts like a spring for applying a force to keep physical contact between the rim and the skin around the eye.

15. The eye examining system of claim 1, wherein the rim of the contact arrangement includes a removing structure that comprises an extension projecting outwards from one location of the rim.

16. The eye examining system of claim 15, wherein the removing structure has a shape selected from the group consisting of: circular shaped, rectangular shaped and triangular shaped.

17. A method of contacting between an eye and an eye examining instrument, the method comprising:
providing a pile of stacked contact arrangements;
contacting between an eye and an eye examining instrument with a contact arrangement located between an eye that is examined and a section of the eye examining instrument, the section being directed towards the eye that is examined;
attaching a second side of one the contact arrangement located in the pile of contact arrangements with a counterpart of the eye examining instrument in a tool-free manner without touching with hands to the contact arrangement and lifting the one contact arrangement from the pile of stacked contact arrangements without touching with hands to the contact arrangement, the attachment being releasable, at the a section of the eye examining instrument, which is directed toward the eye that is examined;
setting a first side of the contact arrangement in contact with the skin around the eye;
applying the second side of the contact arrangement, which is disposable, biocompatible with skin and made of biodegradable material, and comprises a rim around an aperture, through which an examination of the eye is performed, to an eyecup arrangement that comprises the counterpart of the eye examining instrument and that is the section directed toward the eye that is examined, wherein the contact arrangement is formed of porous and waterstable cellulose;

adapting the rim, which is flexible in order to alter its shape under pressure and includes at least one air hole that is configured to let air move in and out of the aperture, to a shape of a surface of the skin around the eye; and wherein the step of attaching the second side of the contact arrangement with the counterpart of the eye examining instrument comprises the step of causing an attachment between the second side of the contact arrangement by causing, by the wall structure, the aperture, together with its counterpart, to overlap with the hole of the eyecup arrangement in response to contact therebetween, examination of the eye being performed through the hole of the eyecup arrangement, the aperture of the contact arrangement having a same shape as the hole through the eyecup arrangement, and the aperture having an area that is smaller than or equal to that of the hole of the eyecup arrangement.

* * * * *